(12) United States Patent
Hegde et al.

(10) Patent No.: US 6,231,543 B1
(45) Date of Patent: May 15, 2001

(54) SINGLE LUMEN BALLOON CATHETER

(75) Inventors: Anant V. Hegde, Newark; Arlene L. Errazo, Sunnyvale, both of CA (US)

(73) Assignee: Intella Interventional Systems, Inc., Sunnyvale, CA (US)

( * ) Notice: Subject to any disclaimer, the term of this patent is extended or adjusted under 35 U.S.C. 154(b) by 0 days.

(21) Appl. No.: 09/292,545

(22) Filed: Apr. 15, 1999

(51) Int. Cl.[7] .................................................. A61M 29/00
(52) U.S. Cl. ........................................ 604/96.01; 606/192
(58) Field of Search ................................ 604/96, 99, 101, 604/103, 523, 528, 532; 606/192–194

(56) References Cited

U.S. PATENT DOCUMENTS

| | | | |
|---|---|---|---|
| 4,932,959 | 6/1990 | Horzewski et al. | 606/194 |
| 5,032,113 | 7/1991 | Burns | 604/96 |
| 5,085,636 | 2/1992 | Burns | 604/99 |
| 5,217,434 | 6/1993 | Arney | 604/99 |
| 5,324,259 | 6/1994 | Taylor et al. | 604/96 |
| 5,437,632 | 8/1995 | Engelson | 604/53 |
| 5,454,788 | * 10/1995 | Walker et al. | 604/96 |
| 5,476,477 | 12/1995 | Burns | 606/194 |
| 5,484,408 | 1/1996 | Burns | 604/96 |
| 5,531,689 | 7/1996 | Burns et al. | 604/99 |
| 5,569,201 | 10/1996 | Burns | 604/96 |
| 5,676,654 | * 10/1997 | Ellis et al. | 606/194 X |
| 5,749,849 | 5/1998 | Engelson | 604/53 |

FOREIGN PATENT DOCUMENTS

| | | | |
|---|---|---|---|
| 0371486 A1 | 11/1989 | (EP) | A61M/25/01 |
| 0462482 A1 | 6/1991 | (EP) | A61M/29/02 |

* cited by examiner

*Primary Examiner*—John D. Yasko
(74) *Attorney, Agent, or Firm*—Limbach & Limbach LLP

(57) ABSTRACT

A dilation catheter having a catheter shaft with an inner lumen for receiving a guidewire and an inflatable balloon member located at the distal portion of the shaft in fluid communication with the inner lumen. The catheter includes a distal seal disposed within the inner lumen of the shaft. The distal seal allows for movement of the guidewire relative to the inner lumen, while also providing for a fluid tight seal around the guidewire, independent of fluid pressure within the lumen, thereby both restricting a patient's blood from passing into the inner lumen and restricting media from the inner lumen from passing into the patient's bloodstream. A valve is located along the catheter shaft and adapted to engage the guidewire and provide for a fluid tight seal around the guidewire when fluid under pressure is applied to the interior of the balloon member. The valve can be surrounded by a perforated rigid sleeve connected to the shaft to provide additional structural support for the shaft at the valve location. As fluid pressure builds in the balloon, the valve is activated against the guidewire to form an additional fluid tight seal around the guidewire.

22 Claims, 2 Drawing Sheets

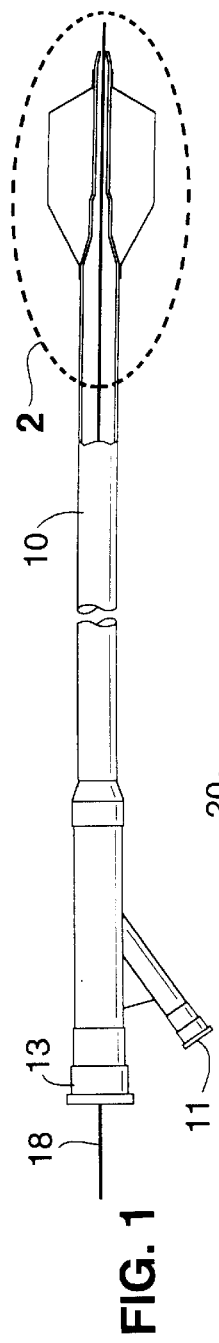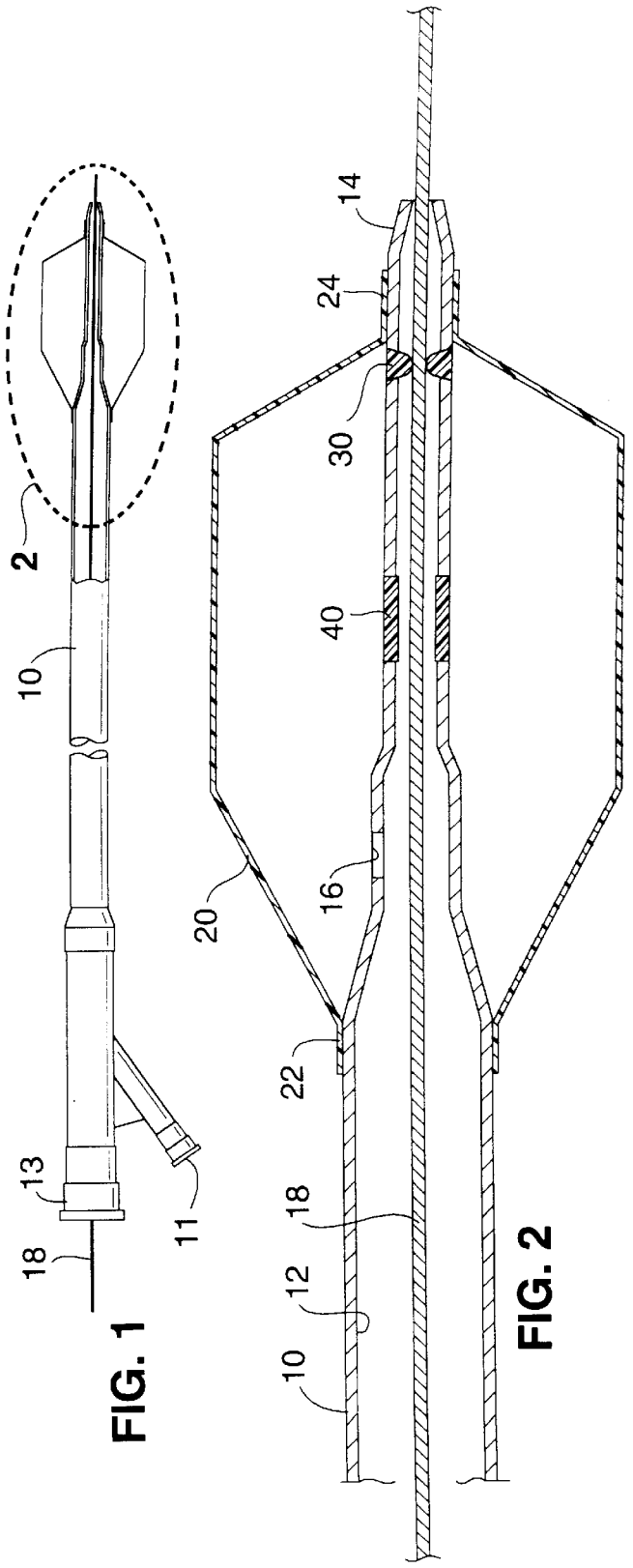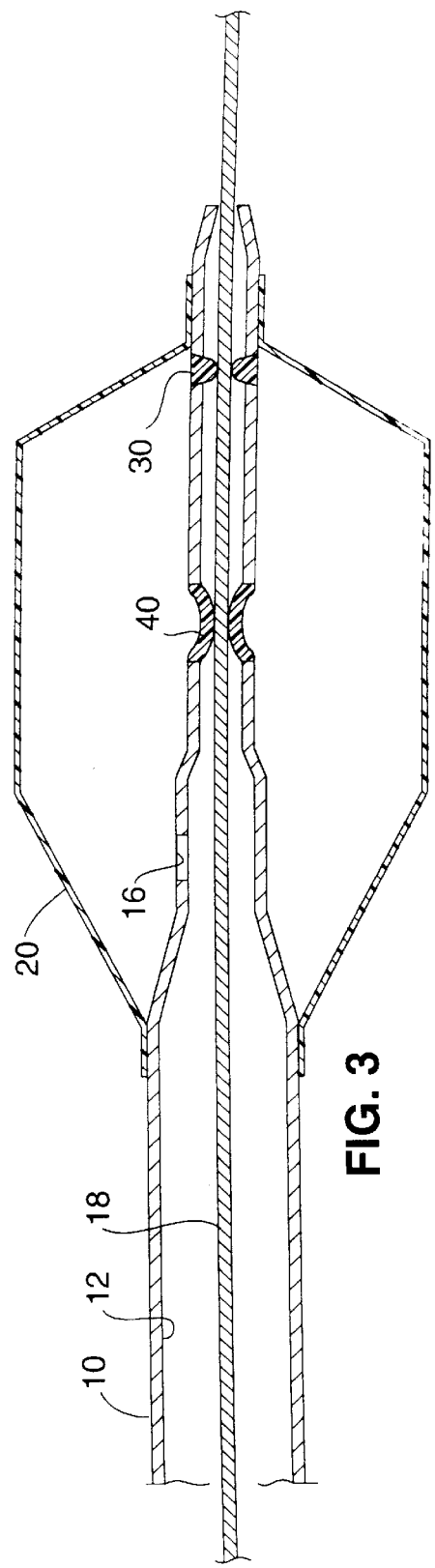

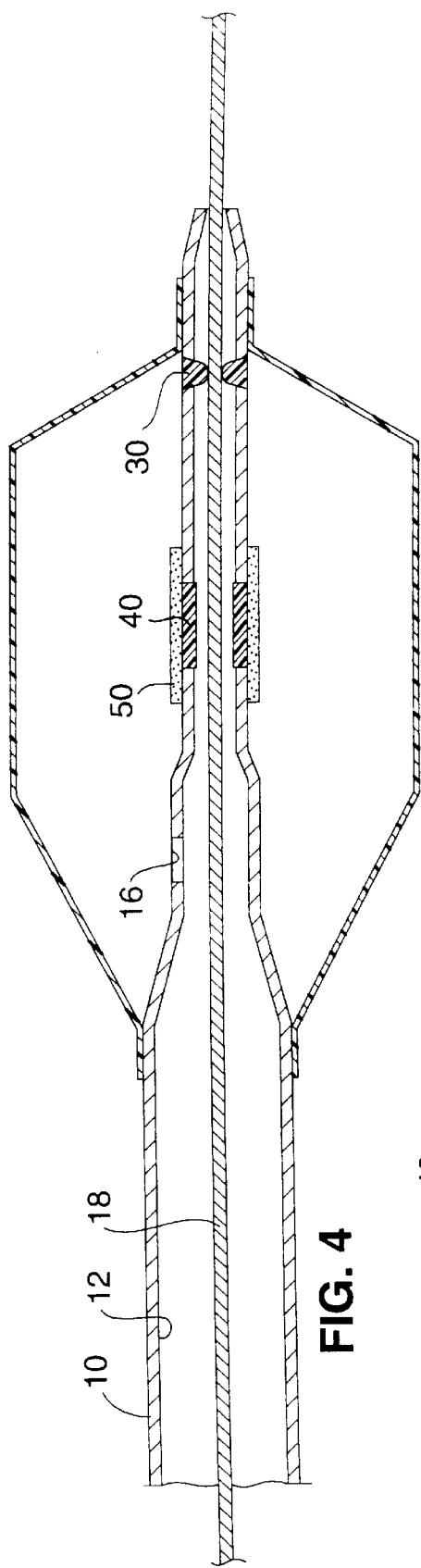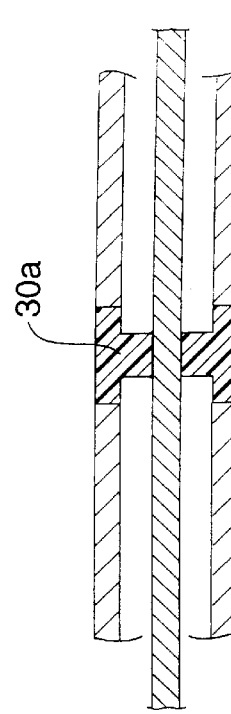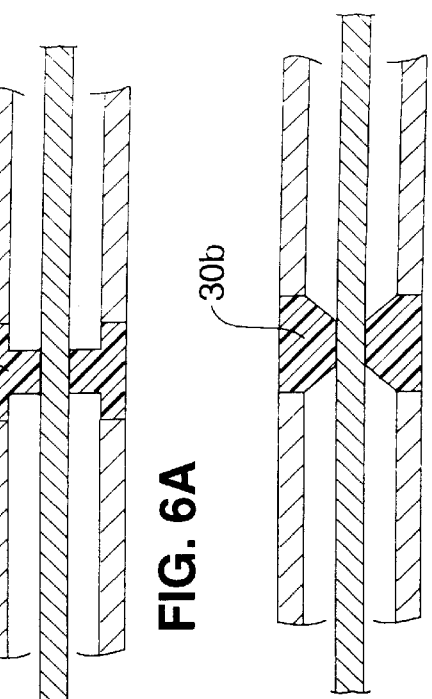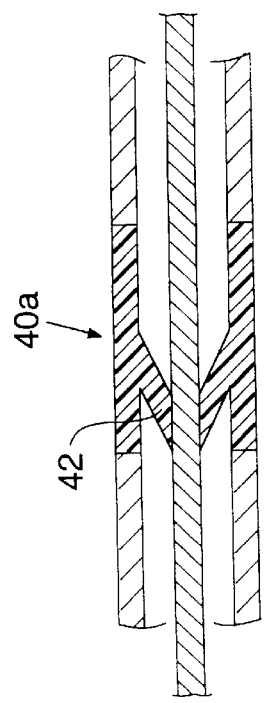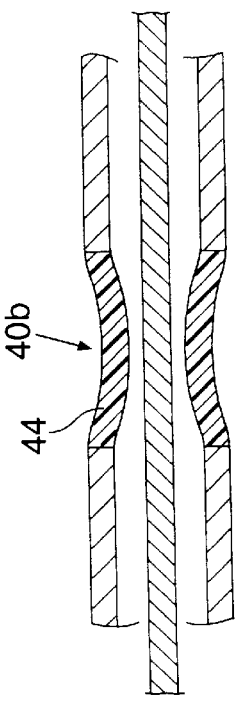

SINGLE LUMEN BALLOON CATHETER

BACKGROUND OF THE INVENTION

1. Field of the Invention

The present invention relates generally to intravascular catheters, and more particularly to balloon dilation catheters suitable for angioplasty procedures.

2. Description of the Related Art

Balloon dilation catheters can be used in a variety of medical procedures and are most widely associated with percutaneous transluminal coronary angioplasty (PTCA). This procedure typically involves introducing a balloon dilation catheter into a patient's vascular system and advancing the catheter to a stenosis or other blockage site within a coronary artery. The balloon is then inflated by supplying fluid under pressure to the balloon. The inflation of the balloon stretches the artery, thereby dilating the stenosed region and restoring the diameter of the artery for increased blood flow.

One or multiple dilations may be necessary to effectively dilate the artery. In many instances, multiple dilations using multiple "over-the-wire" catheters having balloons with increasingly larger diameters may be required. An over-the-wire catheter is one where a separate guidewire lumen is provided so that the catheter can be guided to the stenosis site by running the catheter along the guidewire. In a typical procedure, a physician will first insert and advance a guidewire to the stenosis site. An initial over-the-wire balloon dilation catheter having a fairly small diameter balloon is then passed over the guidewire to the site and the balloon is inflated to partially dilate the vessel, then deflated and the catheter withdrawn. Progressively larger balloon catheters are then advanced to the stenosis along the guidewire, inflated, deflated, and then withdrawn in succession to sufficiently enlarge the opening.

In order to treat stenoses in small arteries, or to treat stenoses having small diameter openings, there have been continuing efforts to reduce the profile of balloon dilation catheters. One disadvantage of over-the-wire balloon dilation catheters is that the overall profile of these catheters is limited due to the provision of both a guidewire lumen and an inflation lumen for inflating the balloon catheter. So-called "fixed wire" catheters have been developed that provide for a lower profile. These catheters are generally fixed to a guidewire or guiding member for advancement to a site of stenosis advance and therefore a guidewire lumen for relative movement between the guidewire and catheter is not required, allowing for a reduced profile relative to an over-the-wire catheter. The lower profile allows these catheters to cross tighter lesions and to generally be advanced deeper into coronary vasculature. The disadvantage of such catheters is that the physician is unable to maintain position at the stenosis site when withdrawing the catheter and replacing it with one having a different balloon diameter. Instead, the path to the stenosis must be continually reestablished.

Therefore, a need exists for reduced profile dilation catheters that can be advanced over a guidewire positioned at a stenosis site. A further need exists for such catheters that are easily manufactured, durable and easy to use.

SUMMARY OF THE INVENTION

The present invention meets the above needs and is directed to a dilation catheter having a catheter shaft with an inner lumen for receiving a guidewire, and an inflatable balloon member located at the distal portion of the shaft and in fluid communication with the inner lumen. A seal is disposed within the inner lumen of the shaft that allows for movement of the guidewire relative to the inner lumen, while also providing for a fluid tight seal around the guidewire independent of fluid pressure within the lumen. A valve is located along the catheter shaft and is adapted to engage the guidewire and provide for a fluid tight seal around the guidewire when fluid under pressure is applied to the interior of the balloon member. The seal is preferably located at the distal portion of the shaft, and in one embodiment of the invention, can be located at the distal tip of the shaft itself. In a preferred embodiment of the invention, the valve is located proximal to the seal.

In another preferred embodiment of the invention, the valve includes a tubular member formed of elastomeric material. As fluid pressure builds in the balloon, the tubular member deflects and compresses against the guidewire to form a fluid tight seal around the guidewire.

In yet another preferred embodiment of the invention, a perforated rigid sleeve surrounds the tubular member and is connected to the shaft. The rigidity of the sleeve provides structural support for the shaft in the region of the tubular member. The perforations provide for fluid communication between the interior of the balloon and the tubular element, thereby allowing the tubular member to deflect and compress against the guidewire when fluid under pressure is introduced into interior of the balloon. In a modification of this embodiment, a radiopaque marker can be incorporated directly into the sleeve to aid in visualization of the catheter tip during use.

In operation, the catheter of the present invention is advanced over a guidewire positioned at a stenosis site. The seal maintains a fluid tight seal around the guidewire while allowing movement of the catheter over the wire. By maintaining a fluid tight seal around the guidewire, the seal operates to keep the patient's bodily fluids, i.e., blood, from entering the catheter lumen. The introduction of blood into the lumen can greatly reduce the effectiveness and lifespan of a catheter. Once blood is introduced into the lumen, it often will tend to coagulate and foul the inner lumen, thereby impeding the passage of the catheter over the guidewire. In addition, such fouling limits the potential reusability of the catheter. By restricting entry of blood into the inner lumen, the seal allows for ease of use and longevity of the catheter of the present invention.

By providing a fluid tight seal around the guidewire, the seal also prevents air or other media within the lumen from entering a patient's blood stream, a potentially harmful occurrence, as the catheter is advanced over the guidewire to the site of dilation. Once the catheter is positioned at the stenosis site, the seal operates in concert with the valve to prevent inflation media from entering the patient's bloodstream upon inflation of the balloon. As the balloon is inflated, fluid pressure in the balloon interior builds and deflects the valve into sealing engagement with the guidewire, thus strengthening the overall fluid tight seal around the guidewire as fluid pressure in the lumen increases.

These and other features, aspects and advantages of the present invention will become better understood with reference to the following description, appended claims and accompanying drawings.

BRIEF DESCRIPTION OF THE DRAWINGS

FIG. 1 is a sectional view of an embodiment of a balloon dilation catheter according to the present invention;

FIG. 2 is an enlarged sectional view of the catheter of FIG. 1, showing the valve and seal, with the valve under zero pressure;

FIG. 3 shows the catheter of FIG. 2 with the valve under positive pressure;

FIG. 4 shows another embodiment of a catheter according to the present invention;

FIGS. 5A–5B show alternative configurations of the valve of FIG. 2; and

FIGS. 6A–6B show alternative configurations of the seal of FIG. 2.

DETAILED DESCRIPTION OF THE PREFERRED EMBODIMENTS

FIGS. 1–2 illustrate one embodiment of a catheter assembly according to the present invention having catheter shaft 10, inflatable balloon member 20, seal 30 and valve 40.

Catheter shaft 10 is an elongated flexible tube having inner lumen 12 that extends through the shaft and opens at the distal tip 14. The lumen extends to the proximal portion of the catheter assembly and connects to an inflation/deflation port 11. Guidewire 18 is disposed within inner lumen 12 and extends therethrough, proximally through guidewire port 13 and distally through distal tip 14. The catheter shaft 10 includes balloon inflation port 16 to provide for fluid communication between inner lumen 12 and the interior of balloon member 20. The catheter shaft itself may be formed of any suitable material known in the art that is sufficiently rigid yet flexible enough to be advanced through coronary vessels while avoiding trauma to the vessels. Preferably, the shaft is made of a polymer, such as polyimide, polyester, nylon, polyethylene, or polyketones. The shaft can also be made of composites. The shaft may optionally be coated with a low-friction material or materials to facilitate advancement through coronary vessels. The most preferred material for the shaft are polyketones of the kind described in U.S. Ser. No. 08/989,791, filed Dec. 12, 1997, U.S. Ser. No. 09/045,483, filed Mar. 20, 1998 and U.S. Ser. No. 09/173,857, filed Oct. 16, 1998, each of which is incorporated herein by reference.

It is generally preferred that the catheter shaft is narrow in diameter to provide for a low profile configuration. Typically, the outside diameter of the shaft is between about 0.020 inches (1.5 F) to about 0.035 inches (2.7 F) and more preferably about 0.022 inches (1.7 F) to about 0.025 inches (1.9 F). To further maintain a low profile, shaft 10 can be necked at the distal end for attachment of balloon member 20, as depicted in FIG. 2. The diameter of inner lumen 12 is larger than that of guidewire 18 to accommodate movement of the guidewire relative to the catheter shaft. The preferred diameter of inner lumen is about 0.016 inches (1.2 F) to about 0.019 inches (1.4 F). Ideally, the distal portion of shaft 10 is about 0.023 inches (1.8 F) in outside diameter with an inner lumen diameter of about 0.017 inches (1.3 F), in order to provide for a catheter shaft with a very low profile and good shaft strength, while still accommodating a 1.2 F or smaller guidewire.

Inflatable balloon member 20 likewise can be formed of suitable material know in the art, preferably polymeric materials including non-compliant materials, such as polyethylene and polyethylene terephthalate, and semi-compliant materials such as Nylon homopolymers and copolymers. The polyketones described above (as described in U.S. Ser. Nos. 08/989,791, 09/045,483, and 09/173,857, incorporated herein by reference) are also useful and can be modified to have non-compliant or semi-compliant properties. The non-compliant or semi-compliant nature of these materials guards against overexpansion of the balloon, which can cause injury to the patient's vasculature. Additives, such as plasticizers and stabilizers, may also be included for manipulating balloon characteristics such as strength and ease of processing. Proximal and distal ends 22 and 24 of balloon member 20 are bonded to shaft 10 by conventional methods, such as thermal bonding, fusing or heat sealing, or adhesive bonding. Thermal fusing methods are preferred because they can yield a lower profile attachment site than adhesive bonding methods, which typically increase the profile of the shaft due to the addition of an adhesive layer between the balloon member and the shaft.

Seal 30 is located at the distal end of catheter shaft 10 and is formed of an elastomeric material and is generally annular in shape having an inner diameter equal to or slightly smaller than the diameter of guidewire 18. The elasticity of the seal should be at least of 90 durometer (shore A) in order for sufficient deflection of the seal to accommodate and seal around the guidewire, and more preferably in the range of 30–50 durometer (shore A). Suitable materials for forming seal 30 include latex, polyurethane, silicone, and other elastomers sold under the trade names KRATON (Shell Chemical, New York, N.Y.), C-FLEX (Concept Polymer, Largo, Fla.) and SANTOPRENE (Monsanto, St. Louis, Mo.). The seal can be formed by casting methods, liquid-injection molding, or other ways generally known in the art. Seal 30 is incorporated into shaft 10 by adhesive bonding or thermal fusing the seal to the shaft. Thermal fusing methods include hot dye or hot air methods, and methods that employ laser energy or radiofrequent energy. In the embodiment shown in FIGS. 1–2, seal 30 is located proximal to distal tip 14 of the shaft. Alternatively, the seal can be located at the distal tip itself. Seal 30 as shown in FIGS. 1–2 is generally annular in shape, and the inner portion of the seal engages guidewire 18 to form a fluid tight seal. The outer portion of the seal is secured to shaft 10. Variations of the seal are shown in FIGS. 6A–6B. In the variation shown in FIG. 6A, the seal 30a has a cross-section that is T-shaped, with the outer portion of the seal having outer rim portions extending both proximally and distally and secured to the shaft. In the variation shown in FIG. 6B, the inner portion of the seal 30b has cross-section that is generally trapezoidal in shape.

Valve 40 is also located at the distal end of the catheter shaft 10, but proximal to seal 30. Valve 40 is formed of an elastomeric material; suitable durometer ratings and materials for forming the valve are the same as those used to form seal 30. The valve is generally tubular in shape, and has an inner diameter greater than the diameter of guidewire 18, allowing the guidewire to freely pass through the valve and inner lumen 12 when the valve is not activated. The elasticity of the valve is such that the valve can deflect into engagement with the guidewire 18. Valve 40 is incorporated into shaft 10, in the same manner as with seal 30, i.e., by thermal fusing or adhesive bonding the valve to the shaft. Variations of the valve are shown in FIGS. 5A–5B. As shown in FIG. 5A, valve 40a is also generally tubular and further includes an annular inner member 42 that extends from the inner wall of valve near the proximal end of the valve which can also engage the guidewire. As depicted, the member terminates at position proximal to its point of attachment to the inner wall of the valve. As shown in FIG. 5B, valve 40b is also generally tubular but the inner diameter of the center portion 44 of the valve is smaller than the inner diameter of either end of the valve.

FIG. 4 shows another embodiment of a catheter assembly according to the present invention. This embodiment further includes sleeve 50 which surrounds valve 40 and is secured to shaft 10 at locations proximal and distal to the valve. The sleeve is of a rigid or semi-rigid material and of sufficient strength to lend structural support to the shaft in the region of the valve. The sleeve is perforated or otherwise porous to allow for fluid communication between the interior of balloon 20 and valve 40. Suitable materials include polymers, such as polyimide, or metals, such as stainless steel. Solid polymers or metals can be perforated, for example, by means of a laser. More preferred rigid sleeves are formed of braided or spiraled (single and double layered) metal wire, which is inherently porous, or slotted metal tubes. Optimally, the rigid sleeve is a slotted metal tube of stainless steel, which combines a high degree of strength and rigidity to lend structural support to the shaft and the desired degree of porosity.

A radiopaque marker can be incorporated directly into the rigid sleeve to provide a visualization aid when using the catheter. For example, for metal sleeves, a radiopaque material can be coated onto the sleeve. Alternatively, the sleeve itself can be formed of metals that are themselves radiopaque, such as platinum, iridium or gold. Where polymers, such as polyimide, are used for the sleeve, the radiopaque materials can be embedded into the polymer material.

In operation, when guidewire 18 is passed through seal 30, the seal stretches and deflects, providing for a fluid tight seal around the guidewire while at the same time still allowing for movement of the guidewire relative to the catheter. When the catheter is introduced into a patient's vasculature, seal 30 prevents blood from entering the portion of inner lumen 12 proximal to the seal. Seal 30, both alone and in concert with valve 40, also prevents inflation media from exiting inner lumen 12 into the patient's body upon inflation of balloon member 20. Importantly, seal 30 operates to achieve a fluid tight seal around guidewire 18 independent of the fluid pressure within the lumen, including positive or negative fluid pressure on one side of the seal relative to the other side. As the typical pressure of blood within a patient's vascular system is approximately 0.2 atmospheres, seal 30 maintains a fluid tight seal around the guidewire up to at least 0.2 atmospheres. Preferably, seal 30 maintains a fluid tight seal around the guidewire up to pressures of at least 1.2 atmospheres, in order to seal against the outflux of inflation media during the initial inflation of balloon member 14 and prior to activation of valve 40.

The valve 40 is activated to provide an additional fluid tight seal around guidewire 18 upon inflation of balloon member 14. In normal use, once the catheter has been positioned at the desired location, inflation of the balloon member dilates a patient's vessel. Inflation of the balloon member is performed by introducing inflation media under pressure into inner lumen 12 through inflation/deflation port 11. Initially, upon the influx of inflation media into inner lumen 12, the inflation media passes through valve 40 until it reaches seal 30. As the media cannot pass through seal 30, due to the fluid tight seal around guidewire 18 provided for by seal 30, the pressure inside the lumen builds and the media enters the interior of balloon member 20 through inflation port 16 and begins to inflate the balloon member. As the fluid pressure inside the balloon member increases, valve 40 deflects and compresses against guidewire 18 to form a fluid tight seal around the guidewire. The valve will initially engage and seal against the guidewire at pressures of at least about 1.0–1.2 atmospheres. Activation of valve 40 by at least this pressure protects against inflation media passing through seal 30 under pressures greater than those that seal 30 can effectively tolerate. The valve continues to seal against the guidewire up to maximum balloon inflation pressures of 14.0 atmospheres or more. The greater the pressure within the balloon member, the stronger the seal against the guidewire.

In the embodiment depicted in FIGS. 1–2, valve 40 is generally tubular in shape. FIG. 3 shows valve 40 in a deflected condition against guidewire 18 and forming a fluid tight seal around the guidewire due to pressure within the balloon interior. Alternative configurations of the valve shown in FIGS. 5A–5B operate in a similar manner. Valve 40a shown in FIG. 5A includes inner member 42 that deflects against the guidewire when inflation media under pressure is introduced into the lumen, thereby enhancing the fluid tight seal around the guidewire. Valve 40b shown in FIG. 5B is configured with center portion 44 of the valve having a smaller inner diameter relative to either end of the valve, thereby positioning the center portion in closer proximity to the guidewire and in turn requiring less overall deflection of the valve in order to engage and seal around the guidewire.

Once dilation of the vessel is completed, balloon member 20 is deflated, typically by applying a vacuum to inflation/deflation port 11. When vacuum is applied, the fluid pressure inside the balloon member decreases. As pressure in the balloon interior falls below 1.0–1.2 atmospheres, the inward deflection of the valve is reduced and the valve disengages from guidewire 18, breaking the fluid tight seal around the guidewire. Once the valve has disengaged from the guidewire, movement of the guidewire relative to the lumen can again occur. Seal 30 continues to provide a fluid tight seal around the guidewire, as interior balloon pressure falls below 1.0–1.2 atmospheres. Seal 30 can further continue to seal against the influx of a patient's blood into the lumen during balloon deflation down to negative lumen pressures of 1.0–1.2 atmospheres. Once the balloon is deflated, the catheter can be advanced further into a patient's cardiovascular system for treatment of additional stenoses, or can be removed from the patient's system.

Although only certain embodiments have been illustrated and described, those having ordinary skill in the art will understand that the invention is not intended to be limited to the specifics of these embodiments, but rather is defined by the accompanying claims.

We claim:

1. A dilation catheter comprising:
   a catheter shaft having proximal and distal ends and an inner lumen extending therethrough for receiving a guidewire;
   an inflatable balloon member at a distal portion of the shaft having an interior in fluid communication with the inner lumen;
   a seal disposed within the inner lumen allowing for movement of the guidewire relative to the inner lumen while providing for a fluid tight seal around the guidewire independent of pressure within the lumen; and
   a valve located along the catheter shaft and adapted to engage the guidewire and provide for a fluid tight seal around the guidewire when fluid under pressure is applied to the interior of the balloon member.

2. The dilation catheter of claim 1 wherein the valve is proximal to the seal.

3. The dilation catheter of claim 1 wherein the seal is at the distal end of the shaft.

4. The dilation catheter of claim 1 wherein said valve comprises a tubular member of elastomeric material.

5. The dilation catheter of claim 4 wherein said tubular member is surrounded by a perforated rigid sleeve.

6. The dilation catheter of claim 5 wherein said rigid sleeve includes a radiopaque marker.

7. A dilation catheter comprising:
 a catheter shaft having proximal and distal ends and an inner lumen extending therethrough for receiving a guidewire;
 an inflatable balloon member at a distal portion of the shaft having an interior in fluid communication with the inner lumen;
 a valve located along the catheter shaft comprising a tubular elastomeric member for engaging the guidewire and providing for a fluid tight seal around the guidewire when fluid under pressure is applied to the interior of the balloon member; and
 a perforated rigid sleeve surrounding the valve and connected to the shaft to provide additional support to the shaft.

8. The dilation catheter of claim 7 further comprising a seal disposed within the inner lumen and allowing for movement of the guidewire relative to the inner lumen while providing for a fluid tight seal around the guidewire independent of pressure within the lumen.

9. The dilation catheter of claim 8 wherein the seal is distal to the valve.

10. The dilation catheter of claim 7 wherein the rigid sleeve includes a radiopaque marker.

11. A dilation catheter assembly comprising:
 a guidewire;
 a catheter shaft having proximal and distal ends and an inner lumen extending therethrough for receiving the guidewire;
 an inflatable balloon member at a distal portion of the shaft having an interior in fluid communication with the inner lumen;
 a seal disposed within the inner lumen and allowing for movement of the guidewire relative to the inner lumen while providing for a fluid tight seal around the guidewire independent of pressure within the lumen; and
 a valve located along the catheter shaft and adapted to engage the guidewire and provide for a fluid tight seal around the guidewire when fluid under pressure is applied to the interior of the balloon member.

12. The dilation catheter assembly of claim 11 wherein the valve is proximal to the seal.

13. The dilation catheter of claim 11 wherein the seal is at the distal end of the shaft.

14. The dilation catheter assembly of claim 11 wherein said valve comprises a tubular member of elastomeric material.

15. The dilation catheter assembly of claim 14 wherein said tubular member is surrounded by a perforated rigid sleeve connected to the shaft to provide additional support to the shaft.

16. The dilation catheter assembly of claim 15 wherein the rigid sleeve includes a radiopaque marker.

17. A dilation catheter assembly comprising:
 a guidewire;
 a catheter shaft having proximal and distal ends and an inner lumen extending therethrough for receiving the guidewire;
 an inflatable balloon member at a distal portion of the shaft having an interior in fluid communication with the inner lumen;
 a valve located along the catheter shaft comprising a tubular elastomeric member for engaging the guidewire and providing for a fluid tight seal around the guidewire when fluid under pressure is applied to the interior of the balloon member; and
 a perforated rigid sleeve surrounding the valve and connected to the shaft to provide additional support to the shaft.

18. The dilation catheter assembly of claim 17 further comprising a seal disposed within the inner lumen distal to the valve and allowing for movement of the guidewire relative to the inner lumen while providing for a fluid tight seal around the guidewire independent of pressure within the lumen.

19. The dilation catheter assembly of claim 18 wherein the seal is distal to the valve.

20. The dilation catheter assembly of claim 18 wherein the seal is at the distal end of the shaft.

21. The dilation catheter assembly of claim 17 wherein the rigid sleeve includes a radiopaque marker.

22. A dilation catheter comprising:
 a catheter shaft having proximal and distal ends and an inner lumen extending therethrough for receiving a guidewire;
 an inflatable balloon member at a distal portion of the shaft having an interior in fluid communication with the inner lumen;
 first means for providing a fluid tight seal around the guidewire independent of pressure within the lumen and for allowing movement of the guidewire relative to the lumen; and
 second means for providing a fluid tight seal around the guidewire when fluid under pressure is applied to the interior of the balloon member.

* * * * *